United States Patent
Aelion et al.

(10) Patent No.: US 9,260,666 B2
(45) Date of Patent: Feb. 16, 2016

(54) METHOD FOR REDUCING THE CARBON FOOTPRINT OF A CONVERSION PROCESS

(71) Applicant: Cool Planet Energy Systems, Inc., Camarillo, CA (US)

(72) Inventors: Vital Aelion, Denver, CO (US); Daren Daugaard, Camarillo, CA (US); Wilson Hago, Camarillo, CA (US)

(73) Assignee: Cool Planet Energy Systems, Inc., Greenwood Village, CO (US)

( * ) Notice: Subject to any disclaimer, the term of this patent is extended or adjusted under 35 U.S.C. 154(b) by 224 days.

(21) Appl. No.: 14/139,151

(22) Filed: Dec. 23, 2013

(65) Prior Publication Data

US 2014/0109638 A1 Apr. 24, 2014

Related U.S. Application Data (63) Continuation-in-part of application No. 14/036,480, filed on Sep. 25, 2013, which is a continuation of application No. 13/189,709, filed on Jul. 25, 2011, now Pat. No. 8,568,493.

(51) Int. Cl.

| | |
|---|---|
| *C10L 5/40* | (2006.01) |
| *C10G 1/00* | (2006.01) |
| *C05F 11/00* | (2006.01) |
| *C07C 1/02* | (2006.01) |
| *C25B 1/00* | (2006.01) |
| *C10G 2/00* | (2006.01) |
| *C10J 3/02* | (2006.01) |
| *C05F 9/04* | (2006.01) |
| *C05F 11/02* | (2006.01) |
| *C10L 1/04* | (2006.01) |
| *C10J 3/62* | (2006.01) |
| *C10B 53/02* | (2006.01) |
| *C10L 5/44* | (2006.01) |

(52) U.S. Cl.
CPC . *C10G 1/002* (2013.01); *C05F 9/04* (2013.01); *C05F 11/00* (2013.01); *C05F 11/02* (2013.01); *C07C 1/02* (2013.01); *C10B 53/02* (2013.01); *C10G 2/00* (2013.01); *C10G 2/30* (2013.01); *C10J 3/02* (2013.01); *C10J 3/62* (2013.01); *C10L 1/04* (2013.01); *C25B 1/00* (2013.01); *C10J 2300/092* (2013.01); *C10J 2300/0916* (2013.01); *C10J 2300/1612* (2013.01); *C10J 2300/1631* (2013.01); *C10J 2300/1671* (2013.01); *C10L 5/447* (2013.01); *Y02E 50/10* (2013.01); *Y02E 50/30* (2013.01); *Y02E 50/343* (2013.01); *Y02W 30/47* (2015.05)

(58) Field of Classification Search
CPC ............ C10G 1/002; C10G 2/00; C10G 2/30; C05F 11/00; C05F 9/04; C05F 11/02; C07C 1/02; C25B 1/00; C10J 3/02; C10J 13/62; C10J 2300/0916; C10L 1/04; C10L 5/447; C10B 53/02; Y02E 50/30; Y02E 50/10
See application file for complete search history.

(56) References Cited

U.S. PATENT DOCUMENTS

| | | |
|---|---|---|
| 203,016 A | 4/1878 | Edison |
| 222,390 A | 12/1879 | Edison |
| 474,230 A | 5/1892 | Edison |
| 4,268,275 A | 5/1981 | Chittick |
| 4,421,524 A | 12/1983 | Chittick |
| 4,487,958 A | 12/1984 | Ream et al. |
| 4,497,637 A | 2/1985 | Purdy et al. |
| 4,530,702 A | 7/1985 | Fetters et al. |
| 4,861,351 A | 8/1989 | Nicholas et al. |
| 4,992,480 A | 2/1991 | Mahajan et al. |
| 5,032,618 A | 7/1991 | Marchionna et al. |
| 5,087,786 A | 2/1992 | Nubel et al. |
| 5,221,290 A | 6/1993 | Dell |
| 5,504,259 A | 4/1996 | Diebold et al. |
| 5,756,194 A | 5/1998 | Shogren et al. |
| 5,820,640 A | 10/1998 | Ikura et al. |
| 5,857,807 A | 1/1999 | Longo, Sr. |
| 6,133,328 A | 10/2000 | Lightner |
| 6,227,473 B1 | 5/2001 | Arnold |
| 6,228,806 B1 | 5/2001 | Mehta |
| 6,339,031 B1 | 1/2002 | Tan |
| 6,548,026 B1 | 4/2003 | Dales et al. |
| 6,747,067 B2 | 6/2004 | Melnichuk et al. |
| 6,811,703 B2 | 11/2004 | Elliott |
| 6,841,085 B2 | 1/2005 | Werpy et al. |

(Continued)

FOREIGN PATENT DOCUMENTS

| | | |
|---|---|---|
| KR | 100819505 | 3/2008 |
| WO | WO-2009004652 A1 | 1/2009 |

OTHER PUBLICATIONS

Buerschaper, R., "Thermal & Electrical Conductivity of Graphite & Carbon at Low Temperatures," Jour. of App. Physics, pp. 452-454 (1944).

(Continued)

*Primary Examiner* — Cephia D Toomer
(74) *Attorney, Agent, or Firm* — Wilmer Cutler Pickering Hale and Dorr LLP (57) ABSTRACT

A method is described for reducing the carbon footprint of any commercially important industrial conversion process. The output of this conversion process can be combustible fuels, chemicals, electricity or heat energy. In its broadest form, a carbon negative module outputs energy to a conversion energy and this energy replaces conventional fossil-fuel based energy. A sequesterable carbonaceous solid is produced by the carbon negative process which represents a net carbon withdrawal from the atmosphere.

24 Claims, 11 Drawing Sheets

(56) References Cited

U.S. PATENT DOCUMENTS

| | | | |
|---|---|---|---|
| 6,923,838 B2 | 8/2005 | Maubert et al. | |
| 6,994,827 B2 | 2/2006 | Safir et al. | |
| 7,033,972 B2 | 4/2006 | Shikada et al. | |
| 7,226,566 B2 | 6/2007 | Beierle | |
| 7,458,999 B2 | 12/2008 | Schenck et al. | |
| 7,846,979 B2 | 12/2010 | Rojey et al. | |
| 7,888,540 B2 | 2/2011 | Deluga et al. | |
| 8,236,085 B1 | 8/2012 | Cheiky et al. | |
| 8,317,891 B1 | 11/2012 | Cheiky et al. | |
| 8,318,997 B2 * | 11/2012 | McAlister | B01J 19/127 201/21 |
| 8,568,493 B2 | 10/2013 | Cheiky et al. | |
| 2003/0119952 A1 | 6/2003 | Werpy et al. | |
| 2004/0111968 A1 | 6/2004 | Day et al. | |
| 2008/0006519 A1 | 1/2008 | Badger | |
| 2008/0093209 A1 | 4/2008 | Noto | |
| 2008/0216391 A1 | 9/2008 | Cortright et al. | |
| 2008/0223269 A1 | 9/2008 | Paoluccio | |
| 2008/0300435 A1 | 12/2008 | Cortright et al. | |
| 2008/0317657 A1 | 12/2008 | Hall et al. | |
| 2009/0007484 A1 | 1/2009 | Smith | |
| 2009/0139139 A1 | 6/2009 | Tilman et al. | |
| 2009/0151251 A1 | 6/2009 | Manzer et al. | |
| 2009/0183430 A1 | 7/2009 | Schubert et al. | |
| 2009/0217575 A1 | 9/2009 | Raman et al. | |
| 2009/0217584 A1 | 9/2009 | Raman et al. | |
| 2009/0253947 A1 | 10/2009 | Brandvold et al. | |
| 2009/0308787 A1 | 12/2009 | O'Connor et al. | |
| 2010/0040510 A1 | 2/2010 | Randhava et al. | |
| 2010/0162780 A1 | 7/2010 | Scharf | |
| 2010/0180805 A1 | 7/2010 | Cheiky | |
| 2010/0218417 A1 | 9/2010 | Bauldreay et al. | |
| 2010/0223839 A1 | 9/2010 | Garcia-Perez et al. | |
| 2010/0257775 A1 | 10/2010 | Cheiky | |
| 2010/0270505 A1 | 10/2010 | Gallaspy et al. | |
| 2010/0300866 A1 | 12/2010 | van Aardt et al. | |
| 2011/0023566 A1 | 2/2011 | Lodwig et al. | |
| 2011/0177466 A1 | 7/2011 | Cheiky | |
| 2011/0209386 A1 | 9/2011 | Cheiky et al. | |
| 2011/0212004 A1 | 9/2011 | Cheiky et al. | |
| 2013/0025188 A1 | 1/2013 | Cheiky et al. | |

OTHER PUBLICATIONS

Cheng, et al., "Stability of Black Carbon in Soils Across a Climatic Gradient," Jour. of Geophysical Research Biogeosciences, vol. 113, G02027, pp. 1-10 (2008).

Chew, T.L. and Bhatia, S., "Catalytic Processes Towards the Production of Biofuels in a Palm Oil and Oil Palm Biomass-based Biorefinery," Bioresource Tech., vol. 99, pp. 7911-8922 (2008).

Demirbas, A., "Effects of Temperature & Particle Size on Bio-Char Yield from Pyrolysis of Agricultural Residues," J. Anal. Pyrolysis, vol. 72, pp. 243-248 (2004).

Elliott, D.C. and Neuenschwander, G.G., "Liquid Fuels by Low-Severity Hydrotreating of Biocrude," Dev. in Thermochemical Biomass Conversion, vol. 1, pp. 611-621 (1996).

Faludi, J.; "World Changing Change Your Thinking a Carbon-Negative Fuel;" Oct. 16, 2007; www.worldchanging.com (9 pgs.).

Gehrer, R. and Hayek, K., "A Fully Programmable System for the Study of Catalytic Gas Reactions," J. Physc. E: Sci. Instrum., vol. 18, pp. 836-838 (1985).

Kim, et al., "Characteristics of Crosslinked Potato Starch & Starch-Filled Linear Low-Density Polyethylene Films," Carbohydrate Polymers, vol. 50, pp. 331-337 (2002).

Laird, D., "The Charcoal Vision: A Win Win Scenario," Agron, J., vol. 100, No. 1, pp. 178-181 (2008).

Lehmann, J., "Nutrient Avail. & Leaching in an Archaeological Anthrosol & Ferraisol of the Central Amazon Basin: Fertilizer, Manure and Charcoal Amendments," Plant Soil, vol. 249, pp. 343-357 (2003).

Lima, et al., "Physiochemical and Adsorption Properties of Fast-Pyrolysis Bio-Chars and their Steam Activated Counterparts," J.Chem. Tech. Biotechnical, vol. 85, pp. 1515-1521 (2010).

Mathews, J.A., "Carbon-negative Biofuels", Energy Policy, vol. 36, pp. 940-945 (2008).

Mohan, et al., "Pyrolysis of Wood/Biomass for Bio-Oil: A Critical Review," Energy & Fuels, vol. 20, pp. 848-889 (2006).

Norman, et al.; "Best Management Practices for Reclaiming Surface Mines in Washington and Oregon," Open-File Report 0-92-2, revised ed. Dec. 1997; www.oregongeology.org Feb. 9, 2010 (128 pgs.).

Ogawa, et al., "Carbon Sequestration by Carbonization of Biomass & Forestation; 3 Case Studies," Mitigation & Adaption Strategies for Global Change, vol. 11, pp. 429-444 (2006).

Omata, et al., "Optimization of Cu Oxide Catalyst for Methanol Synthesis under High C02 Partial Pressure Using Combinatorial Tools," App. Catalyst A: General, vol. 262, pp. 207-214 (2004).

Preston, C.M. and Schmidt, M.W., "Black (Pyrogenic) Carbon; a Synthesis of Current Knowledge & Uncertainties w/Special Consideration of Boreal Regions," Biogeosciences, vol. 3, pp. 397-420 (2006).

Rosenberg, et al., "More on Commercial Carbon Resistors as Low Pressure Gauges," Intl. Jour. of Impat. Eng., vol. 34, pp. 732-742 (2007).

Sharma, R.K. and Bakhshi, N.N., "Catalytic Upgrading of Pyrolysis Oil," Energy & Fuels, vol. 7, pp. 306-314 (1993).

Takeishi, K., "Dimethy Ether & Catalyst Development for Production of Syngas," Biofuels, vol. 1(1), pp. 217-226 (2010).

Tryon, E.H.; "Effect of Charcoal on Certain Physical, Chemical, & Biological Properties of Forest Soils," Ecological Monographs, vol. 18, No. 1, pp. 81-115 (Jan. 1948).

International Search Report and Written Opinion issued by the U.S. Patent and Trademark Office as International Searching Authority for International Application No. PCT/US2012/44240 mailed Aug. 23, 2012 (11 pgs.).

McHenry, Mark P., "Agricultural Bio-char Production, Renewable Energy Generation and Farm Carbon Sequestration in Western Australia: Certainty, Uncertainty and Risk," Agriculture, Ecosystems and Environments, vol. 129, pp. 1-7 (2009).

International Search Report and Written Opinion Issued by the U.S. Patent and Trademark Office as International Searching Authority for International Application No. PCT/US14/72159 mailed Mar. 18, 2015 (11 pgs.).

* cited by examiner

- Total $CO_{2,eq}$: 1002 kg $CO_{2,eq}$/dry tonne of biomass

METHOD FOR REDUCING THE CARBON FOOTPRINT OF A CONVERSION PROCESS

RELATED APPLICATIONS

This application is a continuation in part application to co-pending U.S. application Ser. No. 14/036,480, filed Sep. 25, 2013, which is a continuation of U.S. application Ser. No. 13/189,709, filed Jul. 25, 2011, the contents of which are incorporated by reference in their entirety.

TECHNICAL FIELD

The present invention relates generally to carbon footprint reduction and to methods for effecting this reduction.

BACKGROUND

The atmosphere is being presently overburdened by carbon emissions produced from fossil fuels. The burning of fossil fuels presently contributes to an annual release of 4 billion metric tons of carbon dioxide into the atmosphere and the injection of 2 billion metric tons of carbon dioxide into the world's oceans. It has been well documented that these carbon emissions negatively impact living organisms in the oceans as well as on land. It is desirable to minimize the impact of the fossil fuel emissions.

There is presently interest in producing biofuels from a wide variety of feedstocks, in order to provide suitable replacements for fossil fuels. There is also interest in reducing the carbon footprint of many industrial processes. By carbon footprint of a conversion process is meant the emissions of greenhouse gases generated by the conversion process. It is generally expressed as amount of carbon dioxide equivalents per weight of produced product or produced energy. Carbon dioxide is the primary greenhouse gas considered, although any other greenhouse gases such as nitrogen oxide and methane falls under the category. The carbon footprint generally entails production and consumption of food, fuels, manufactured goods, and materials and services used in the conversion process.

In particular, it is desirable to reduce the carbon footprint of a carbon positive process, or combine any carbon positive process or processes with one or more negative carbon processes to reduce the carbon footprint of a given process. The idea of carbon negative processes in the production of fuels has been previously discussed. See, for example, J. A. Mathews, "*Carbon-negative biofuels*", in *Energy Policy* 36 (2008) pp. 940-945.

Approaches directed toward the production of carbon negative fuels include those described in US Patent Publication 2010/0311157, which teaches the production of biofuels from algae as feedstock. The process is claimed to be carbon negative due to the high absorption of $CO_2$ by the algae. US Patent Publication 2010/0040510 discloses a multistage pressurized fluidized bed gasifier operating between 780° C. and 1100° C. that converts biomass to synthesis gas and biochar. The biochar is said to be capable of being added to soil. The formation of methane, gasoline-like volatiles such as BTX (benzene, toluene, and xylene) and tar is explicitly avoided. The gasifier is said to possibly produce carbon negative fuel. US Patent Publication 2008/0317657 discloses a system and method for sequestering carbon in the form of char created by gasifying biomass in an unspecified reactor vessel. A low heating value producer gas is a by-product of the process. US Patent Publication 2004/0111968 discusses pyrolyzing biomass to produce char and pyrolysis gases which are steam reformed to hydrogen. The char is treated to become a carbon based fertilizer.

SUMMARY

A process by which conversion processes characterized by carbon positive footprints can attain reduced carbon footprints is by insertion of one or more carbon negative processes is described.

In its most general form, the present invention discloses a method for reducing the carbon footprint of any conversion process via the introduction of one or more external carbon negative processes which use renewable inputs.

In one aspect, a method for reducing the carbon footprint of a conversion process includes (a) conducting an external carbon negative process having biomass as input and sequesterable carbon and one or both of renewable energy and renewable feedstock as outputs, and b) utilizing said renewable energy to at least partly power said conversion process and/or utilizing said renewable feedstock as input to said conversion process.

In one or more embodiments, the conversion process includes one or more of: electricity production, electrochemical reduction process, smelting, fossil fuel extraction, chemical refining, chemical conversion processes.

In any preceding embodiment, the renewable energy is selected from the group consisting of heat, combustible biovapors, combustible fuels and electricity.

In any preceding embodiment, electricity is produced by combustion of one or both of combustible biovapors or renewable fuels obtained as output from the carbon negative process.

In any preceding embodiment, the renewable feedstock comprises light hydrocarbons, C1-C5 light gases, or C6-C20 hydrocarbons.

In any preceding embodiment, the sequesterable carbon is greater than 50% fixed carbon.

In any preceding embodiment, the carbon footprint reduction is greater than 1%, or the carbon footprint reduction is greater than 10%.

In any preceding embodiment, the sequesterable carbon is sequestered by use as a soil amendment, and/or the sequesterable carbon is sequestered by underground storage, and/or the sequesterable carbon is sequestered by addition to soil containing compost material.

In any preceding embodiment, the sequesterable carbon is used for carbon offsets and/or the sequesterable carbon is used for carbon credits.

In any preceding embodiment, at least some of the sequesterable carbon is reacted with oxygen, carbon dioxide, methane or steam to generate synthesis gas, which displaces fossil carbon, and for example, the synthesis gas is converted to combustible fuels, refinery stock or chemicals.

In any preceding embodiment, at least one of the combustible fuels, refinery stock or chemicals is certified as carbon negative.

In any preceding embodiment, the output of a plurality of carbon negative processes serve as input to the conversion process.

In any preceding embodiment, the carbon negative process causes the conversion process to qualify for RINs.

In another aspect, a system for reducing the carbon footprint of a conversion process includes (a) an external carbon negative system having biomass as input and sequesterable carbon and one or both of renewable energy and renewable feedstock as outputs to the conversion process; and b) a conversion process directly coupled to the external carbon negative system for receiving one or more of said renewable energy as power in said conversion process and said renewable feedstock as input to said conversion process.

In any preceding embodiment, the size of the carbon negative system is adjustable.

In any preceding embodiment, the carbon negative system produces biochar and biovapors.

In any preceding embodiment, a plurality of external carbon negative system are directly coupled into said conversion process.

In any preceding embodiment, the plurality of external carbon negative systems communicate in parallel with said conversion process.

In any preceding embodiment, the plurality of external carbon negative systems communicate in series with said conversion process.

In one embodiment, the carbon negative process utilizes a pyrolysis process with renewable feedstocks such as wood and grasses. The pyrolysis process produces a carbonaceous solid which can be sequestered in soil for an extended period of time. In one embodiment, the pyrolysis produces energy, for example, in the form of heat, energy or renewable fuel, to render the process energy self-sufficient, producing energy to power the pyrolysis as well as energy to power an external conversion process. In one embodiment, the pyrolysis produces combustible vapors, which are burned to produce electricity that can be used to power devices in the conversion process. In yet another embodiment, the pyrolysis vapors are fed to a catalytic conversion process to produce renewable fuel or chemicals. The renewable fuel can serve as a carbon negative energy source for an external conversion process. Alternatively, or in addition, the renewable chemicals can serve as carbon negative feedstock for an external energy process.

In another embodiment of the invention, a plurality of carbon negative process produce output in parallel, and this output is fed to a conversion process. In another embodiment, the carbon negative processes are linked, such as drying and/or torrefaction, followed by pyrolysis, followed by gasification, and their output is collected and fed to the conversion process. In a still another embodiment, a biofractioning process is the carbon negative process.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION

Embodiments of the invention are directed toward methods for reducing the carbon footprint of any conversion processes, in particular industrial conversion processes having significant carbon positive emissions.

Figure 1:
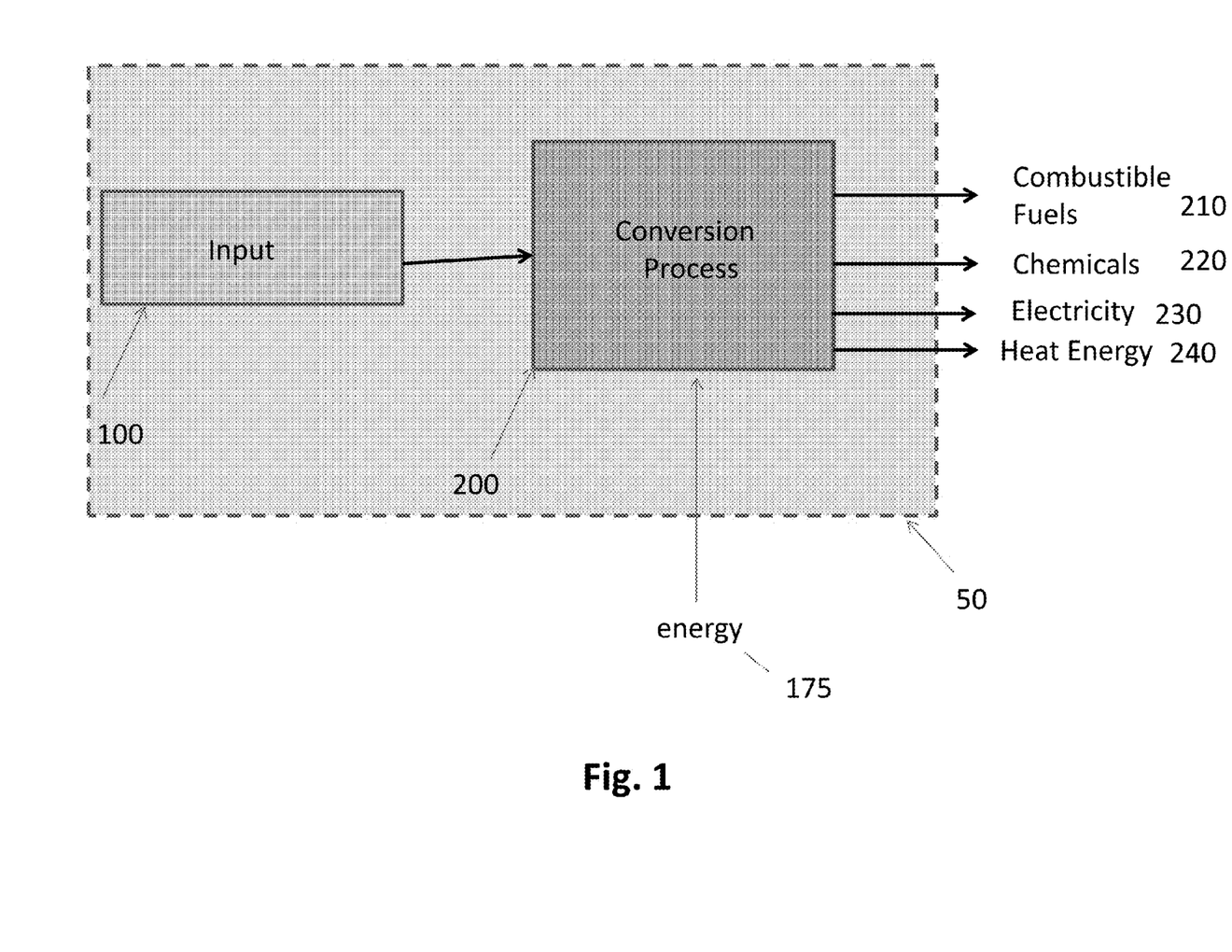
FIG. 1 is a flow diagram illustrating an embodiment of a carbon positive conversion process which takes an input and converts it into at least one of: combustible fuels, chemicals, electricity or heat energy.

A conversion process is defined as a process which uses energy to take an physical input and convert it into at least one of: combustible fuels, chemicals, electricity or heat energy. The latter are referred to as useful products. A conversion process necessarily has two inputs: a physical input and an energy input. In a typical carbon positive process, the physical input is of non-renewable source and the energy input is derived from fossil fuels. The energy input to the conversion process may be electricity or heat energy or other form of energy, such as electrochemical or nuclear, needed to perform the conversion. FIG. 1 is a flow diagram illustrating an embodiment of a production module containing a carbon positive conversion process. Shown is a carbon positive production module 50 comprising an input 100, and conversion process 200. Both input 100 and conversion process 200 have positive carbon footprints, meaning that carbon dioxide was releases/generated to produce them, so that the output of production module is carbon positive. Possible outputs of conversion module are combustible fuels 210, chemicals 220, electricity 230 and heat energy 240. The input 100 can be any substance, of renewable or non-renewable source, carbon containing or not, which is fed to conversion process 200. Embodiment of input 100 include unprocessed ore, raw feedstock, and raw chemicals. The full nature of the embodiments of input 100 will become evident from disclosure of embodiments of conversion process 200.

Conversion process 200 may be applied to chemical and industrial processes that use energy to effect a physical or chemical transformation in feedstock material to a different substance or substances. The conversion process may be applied on its own, or as part of a larger process. Embodiments of particularly high carbon footprint conversion processes include smelting processes which transform ores to metals, as in lead, steel or copper smelting; electrochemical reduction processes from the oxides to metals, as in aluminum oxide reduction to aluminum metal in the Bessemer process, and pyroprocessing methods which use heat to combine materials, such as clay, sand, or cement, or steelmaking processes using oxygen. Processes involving physical formation of a substance are included. Processes involving change of the physical state of a substance, such as liquefaction of gases, gas scrubbing, drying using supercritical means, and freeze drying are also included. Processes involving changes in size of a given substance, as in communition processes, are covered.

Electrolytic processes include plating processes which deposit a material on an electrode, including gilding, anodization, and electrowinning, as well as electrotyping, electro-etching, electro-engraving, electropolishing, electrophoretic and electroseparation processes. Processes using electric arc furnaces are included.

Of physical forming processes, metal fabrication processes involving casting, stamping, machining by large and small machines, forging such as wrought iron forging in furnaces, soldering, metal cutting, metal polishing, processes which harden or render metals more ductile, die making. Also included are molding processes such as compression molding and blow molding. Cleaning processes such as sandblasting, water jet blasting, hot air blasting, and liquid blasting processes are also included.

Physical and chemical separation processes including various forms of distillation such as vacuum and steam distillation, solvent extraction processes such as organic solvent extraction and supercritical extraction, and flotation separation processes are included.

Chemical processes involving the conversion of one chemical into another are covered. Examples of these numerous chemical processes include chemical petroleum or large molecule cracking processes, alkylating processes, benzene functionalization processes, and processes using Friedel-Crafts chemistry. Also included are process which utilize polymerization reactions, benzene functionalization reactions, Diels-Alders reactions, olefin metathesis reactions, transesterification reactions, soap making chemistry, amide formation reactions, carbonylation reactions, and acidification and alkali reactions.

A conversion process as specified above using fossil fuels will generally have a positive carbon footprint. Any of these processes may benefit from the current invention, by coupling the carbon positive footprint process with a carbon negative process, to reduce the carbon footprint of the output. In some cases, the footprint may be so relatively high among comparable other conversion processes as to classify the process as energy intensive. It is particularly for those processes that the present invention demonstrates its utmost utility.

Figure 2:
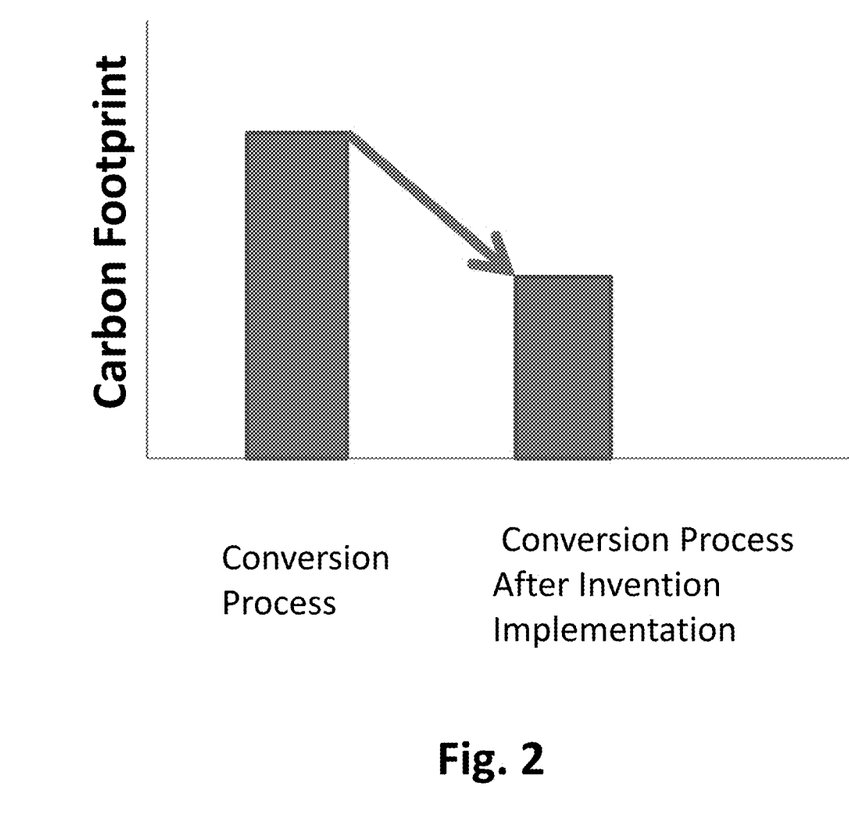
FIG. 2 is an example of the effect of reducing the carbon footprint of a conversion process after implementation of the invention.
Figure 3:
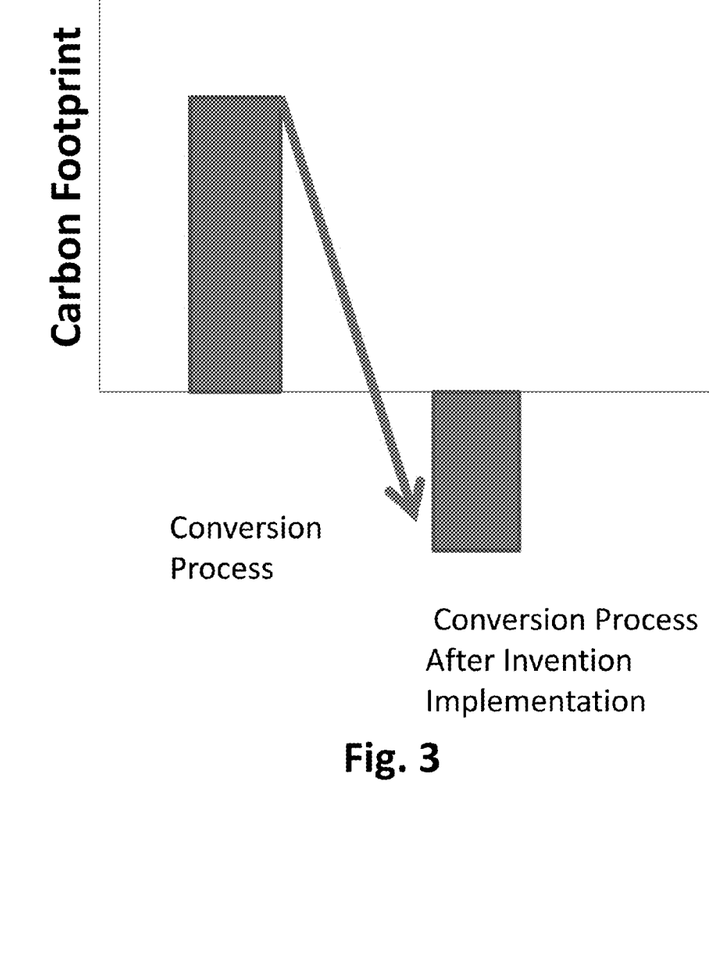
FIG. 3 illustrates the effects of implementing the present invention upon application to a carbon positive conversion process. The carbon footprint of the conversion process is reversed upon invention implementation.
Figure 4:
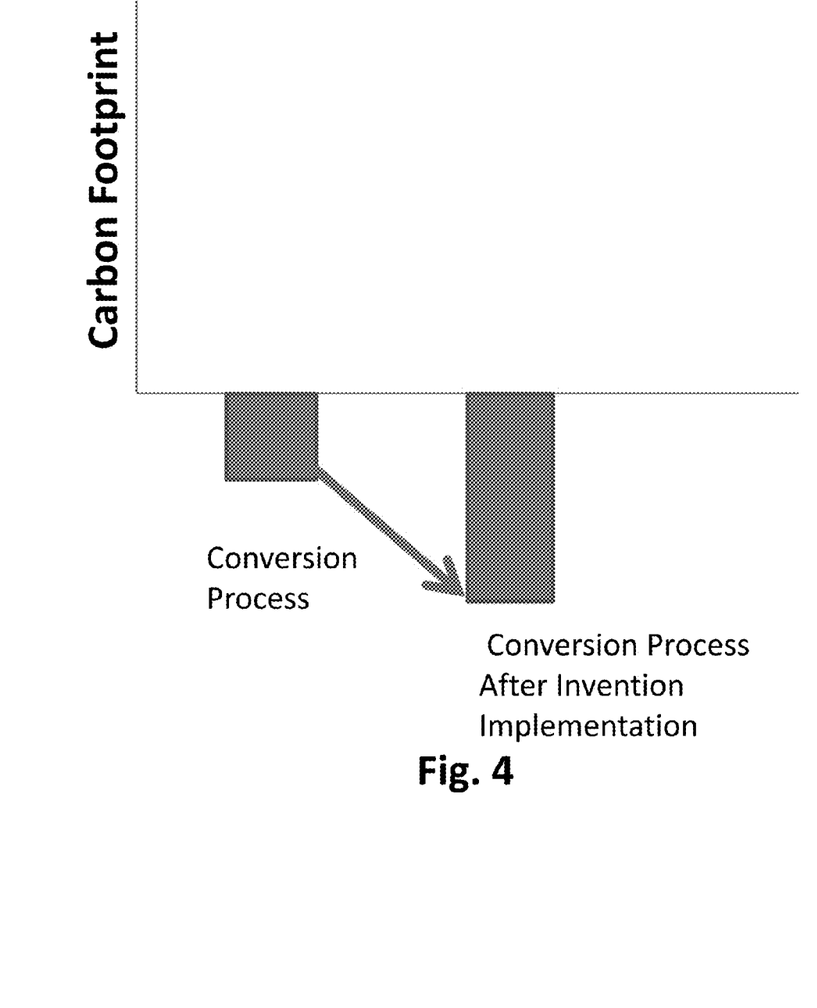
FIG. 4 illustrates the effects of implementing the present invention upon application to a carbon negative conversion process. The carbon footprint of the conversion process is further diminished upon invention implementation.

Implementation of the present invention will serve the purpose of reducing the carbon footprint by virtue of the introduction of a carbon negative process into an energy intensive fossil fuel based conversion process. The effect will be to reduce the footprint as shown in FIG. 2, although in some embodiments the reduction will so significant as to actually render the process overall carbon negative. This is demonstrated in FIG. 3 which illustrates the effect of reversing the carbon footprint from positive to negative. The invention can also be applied to a carbon negative process, in order to render it even more negative. This is illustrated by FIG. 4. The effect of reducing the carbon footprint of a given process will be termed 'carbon remediation' in the present context. The present invention will reduce carbon footprint for any conversion process by more than 1%, and preferably by more than 5%, and most preferably by more than 10%. It may qualify a conversion process for RIN (renewable identification number) credits.

Figure 5:
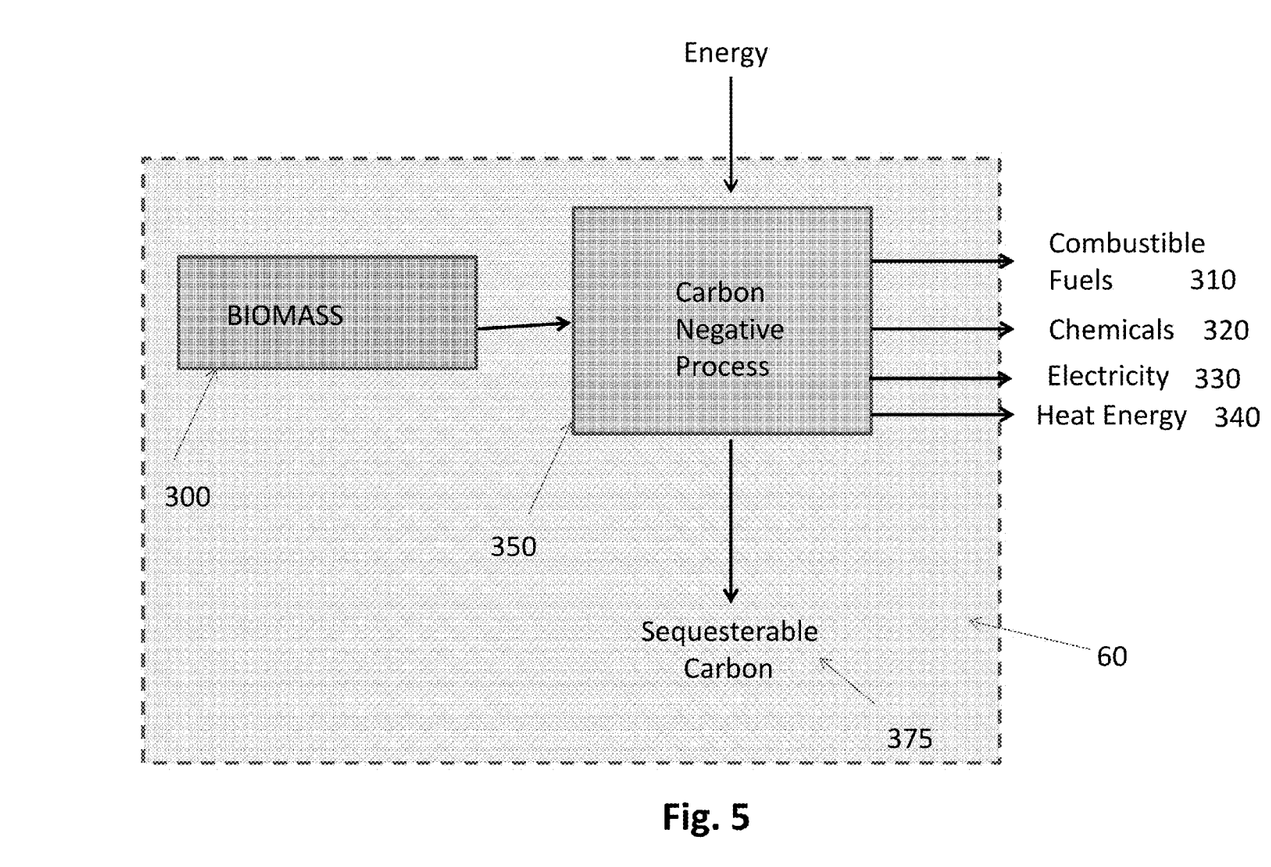
FIG. 5 is an embodiment of a negative carbon process module which has biomass as input and as outputs has a sequesterable carbon and at least one of: combustible fuels, chemicals, electricity or heat energy.

Carbon remediation of a conversion process or production module may be achieved by coupling a carbon negative module to the conversion process. A carbon negative module contains a process that converts a renewable input such as biomass into useful products and in the process sequesters carbon. Due to the carbon fixing of biomass that absorbs large quantities of carbon dioxide, biomass is a highly carbon negative input into the process. An embodiment of a carbon negative module 60 is shown in FIG. 5. A renewable input 300 such as biomass is directed to carbon negative process 350 which produces a carbonaceous sequesterable co-product 375 (often termed biochar). Typically, an energy input is required for the conversion of the biomass. Sequesterable carbon is considered to have a very low footprint, and can be considered to have a 'zero' carbon footprint. The carbon negative process produces one or more of renewable energy or renewable feedstock that can be used in subsequent conversion processes. Outputs from module can include at least one of: combustible chemicals 310, chemicals 320, electricity 330 and heat energy 340. The sequesterable nature of the product 375 enables carbon negativity for module 60. The overall process is carbon negative as long as the highly carbon negative biomass input outweighs the carbon positive external energy sources that are inputs to the carbon negative process 350. The carbon impact of the energy input can be reduced by using a renewable resource (discussed in greater detail below).

Sequesterable carbon is characterized by its recalcitrance to microbial decomposition. It is typically greater than 50% fixed carbon. A sequesterable carbon will exhibit less than 20% microbial decomposition after residence in soil for one year. In other embodiments, a sequesterable carbon will exhibit less than 10% or less than 5% microbial decomposition after residence in soil for one year. In many instances, sequesterable carbon will demonstrate resistance to microbial decomposition for significantly longer times, such as more than 5 years or more than 10 years, or more than 20 years, or more than 50 years. Examples of possible carbon negative processes include thermochemical pyrolysis of biomass, bioenergy production with carbon capture and oil production using algae. In the latter case, the form of carbon capture is gaseous $CO_2$ and algae oil is liquid hydrocarbon (displacing fossil emitted $CO_2$).

Figure 8:
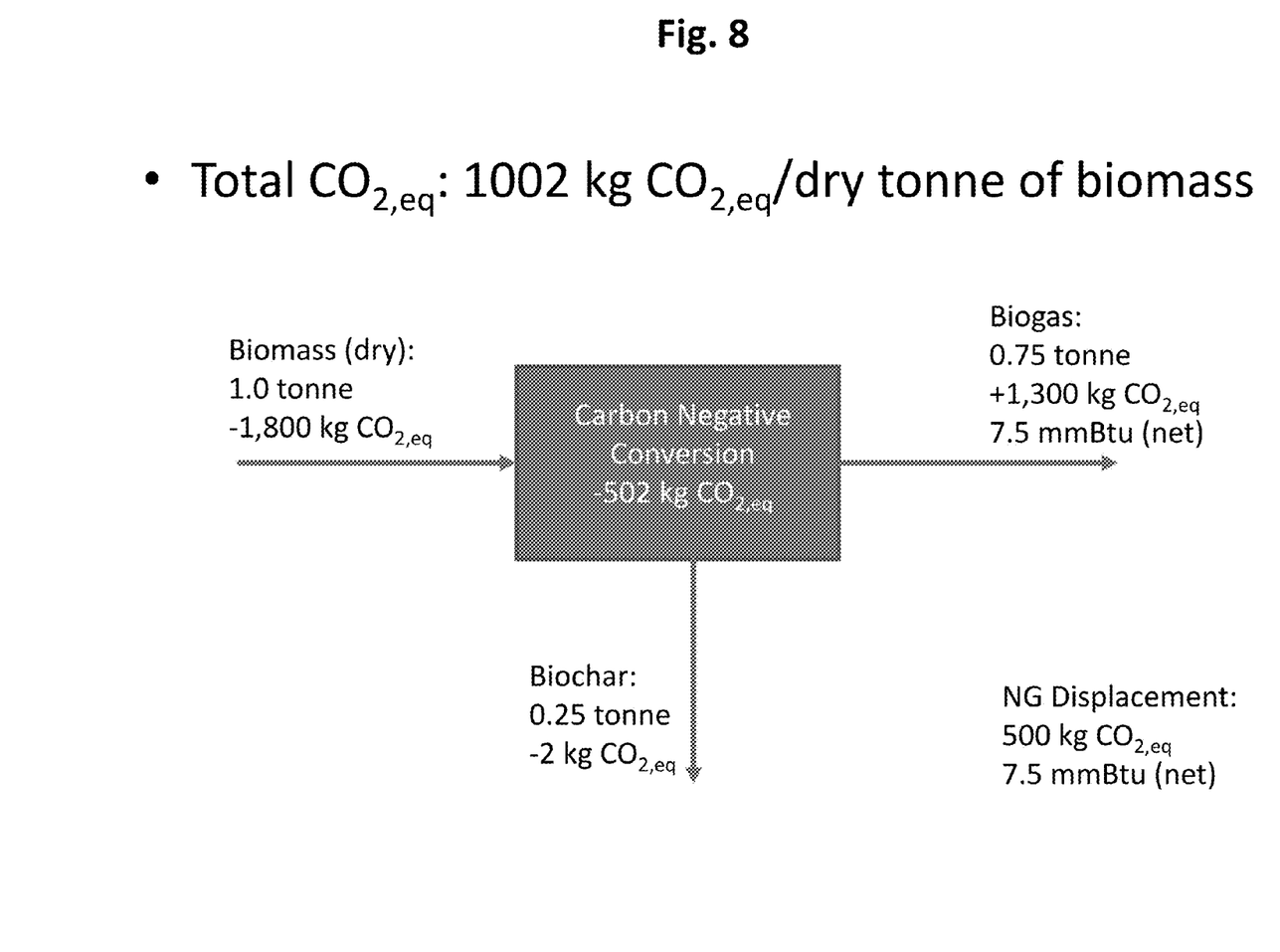
FIG. 8 shows a mass balance for an embodiment of a carbon negative process module with 1.0 ton of biomass as input and 0.25 ton sequesterable char and 0.75 ton biovapors and light gases as output as well as CO2 equivalents distribution.

An embodiment of the carbon negative module 50 is shown in FIG. 8. This a mass and energy balanced process. 1 ton of biomass is introduced into a pyrolysis process which converts it to 0.75 ton of biovapors and light gases and 0.25 ton of biochar. Biovapors include lower molecular weight oxygenated and hydrocarbon compounds generated by the decomposition of biomass. 7.5 mm BTU is net generated and is capable of being sent to a conversion process, such as a smelting process. This energy represents a renewable displacement of 500 kg of $CO_2$ which would have been obtained from combustion of natural gas.

Figure 9:
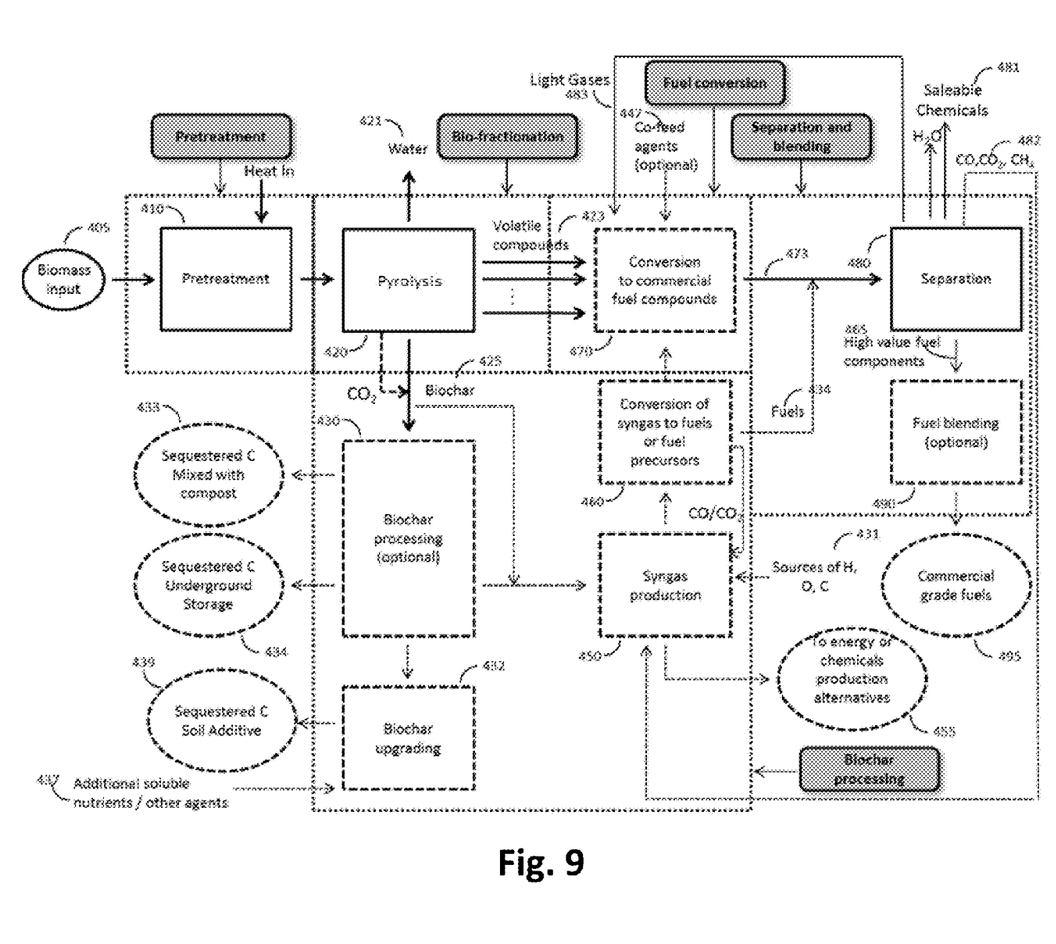
FIG. 9 is an embodiment of a carbon negative process module with more detailed possibilities for biovapor conversion and biochar processing.

In another embodiment of the invention, the carbon remediation may be effected by a more complex process than that depicted in FIG. 8. FIG. 9 illustrates an embodiment of a carbon negative process containing a wide variety of components. The components for this process have been previously disclosed in U.S. Pat. No. 5,568,493 and U.S. Pat. No. 8,430,937, which are incorporated in their entirety by reference. Referring now to FIG. 9, biomass 405 is inputted into pyrolysis process 420 to concurrently produce combustible fuels and chemicals 495 and sequesterable carbon 425. Biomass 405 is pretreated in operation 410 prior to being subjected to the pyrolysis process 420. The conversion process produces sequesterable carbon 425 and volatile gas streams 423, e.g., containing biovapors and light gases.

With continued reference to FIG. 9, the volatile gas streams 423 are transformed to commercial grade fuels 495 via separation and blending processes 480 and 490, respectively, which can also produce saleable chemicals 481 and 491. An optional fuel conversion process 470 converts the volatile gas streams to renewable fuel components 473, which can contain for example acetylene, benzene, toluene and xylenes. The sequesterable char 425 may partly be converted to synthesis gas via syngas production step 450. The synthesis gas can have numerous uses, including conversion to fuels and fuel precursors via process 460, and utilization in energy production or chemical production 455. Synthesis gas production process 450 can receive input from: (i) biochar processing 430, (ii) external sources of hydrogen, carbon or oxygen 431, (iii) recycled carbon monoxide or carbon dioxide from process 460, or (iv) recycled gases after the separation process 482.

In some embodiments, biochar 425 may be sequestered in underground storage product 434. The biochar may also be mixed with compost to yield sequestered product 433. Direct utilization of the biochar as a soil amendment is also possible, since the residence time of biochar in soil is in the order of millennia. The latter has been determined from the persistence of biochar as a soil enhancement agent in Amazonian soil terra preta. Biochar 425 may also be upgraded via different techniques and sold as a soil fertilizer 439 to enhance soil growth. In further embodiments, biochar 425 may optionally be processed prior to being sold directly for various end uses such as activated charcoal, gas purifier, coal purifier and water purifier. Further detail of the biochar processing and sequestration can be found in U.S. Pat. No. 8,430,937, which are incorporated in their entirety by reference. The commercial grade negative carbon fuels 495 arise from the concurrent production of pyrolysis-derived renewable fuels and sequesterable biochar.

With no external energy inputs, the carbon negative module of FIG. 5 is necessarily carbon negative due to the presence of the biochar. Even with the addition of external energy, selection of appropriate energy inputs and recycling of the various outputs of the carbon negative process back into the process also results in a carbon negative process.

Figure 6:
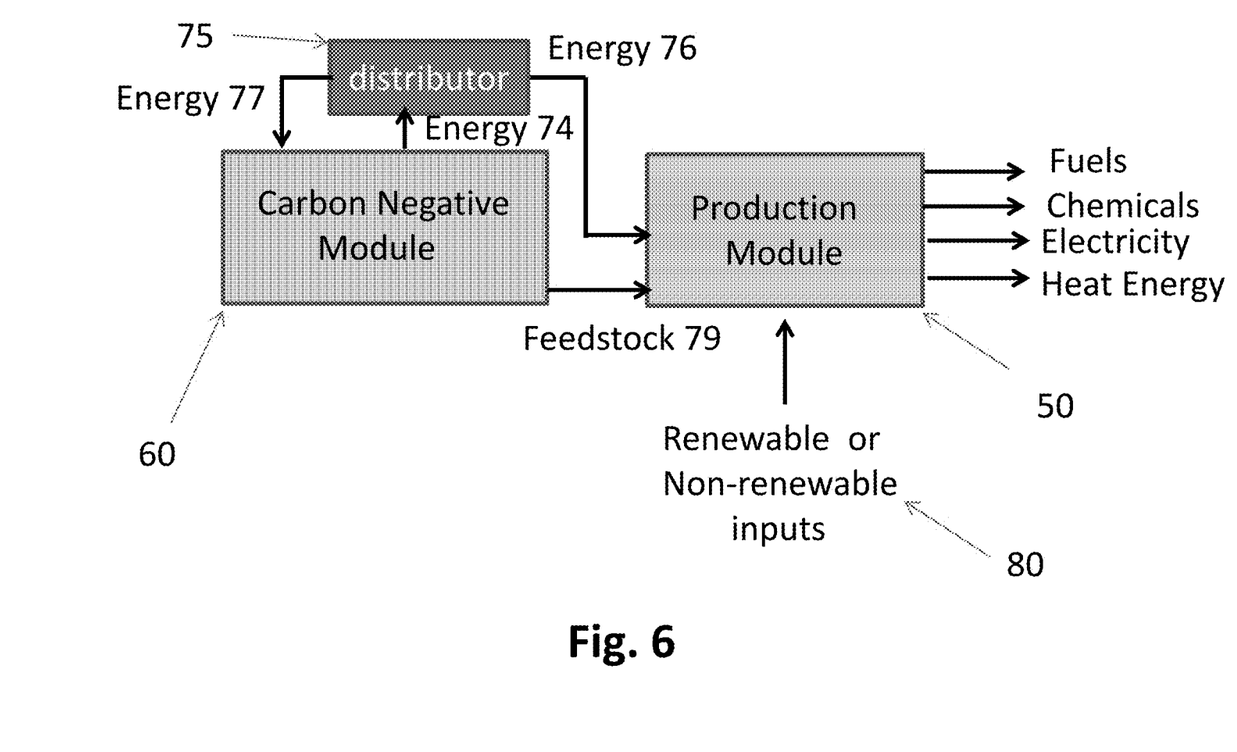
FIG. 6 is a block diagram illustrating an embodiment for inserting a carbon negative process module into a conversion process.

When coupled with a conversion process as shown in the embodiment of FIG. 6, a reduction of the carbon footprint of the conversion process is possible. FIG. 6 shows a carbon negative module 60 coupled to a production module 50 via energy distributor 75. Distributor 75 can comprise a simple tubing with a tee configuration. Energy distributor 75 distributes energy 74 which comes from the carbon negative module. In a biomass pyrolysis process, energy 74 can include pyrolysis energy (heat), heat generated by burning of pyrolysis gases, or electricity production as a result of burning of pyrolysis gases. The energy distributor 75 directs energy, e.g., combustion energy 76 generated from the carbon negative module, to the production module. The combustion energy 76 serves as a source of energy used to supplement or decrease the energy needs of conversion process in the production module. Part of the energy generated by carbon negative module can be diverted (shown as energy 77) to self-energize the carbon negative process, thus further improving carbon negativity of the process by reducing external input energy needs.

As shown in FIG. 5, the carbon negative module can produce useful outputs in the form of carbon negative chemicals, combustible fuels or other forms of materials. This output is shown in FIG. 6 as feedstock 79 for the production module. Feedstock 79 can comprise light hydrocarbons, C1-C5 light gases, or C6-C20 hydrocarbons. In certain embodiments, the feedstock can be used for the generation of heat or electricity that is used in a conversion process, such as smelting or electrochemical reduction processes or any process requiring heat or electricity as part of the conversion process or as energy to drive the conversion process.

Feedstock can also be embodied in a production module involving a chemical conversion process, such as conversion of benzene to benzoic acid in a benzene formylation process. Other exemplary feedstocks from pyrolysis of biomass include acetylene, toluene, xylene and acetic acid, all of which are feedstocks for a variety of chemical production processes. By way of example, toluene can be used as a precursor to benzene and in oxidation reactions to yield benzaldehyde and benzoic acid, two important intermediates in chemistry, acetic acid is a useful reagent for the formation of acetaldehyde, and acetylene can be used as a feedstock with alcohols, hydrogen cyanide, hydrogen chloride, or carboxylic acids to give vinyl compounds and with carbon monoxide to give acrylic acid. Production module 50 may have additional inputs 80, of renewable or non-renewable form, that allows the conversion process to perform the conversion.

In one or more embodiments, the carbon negative module is coupled to the production module. The coupling of the two processes eliminates or reduces the energy required to make the carbon negative renewable resources available for a conversion process. For example, if a conversion process is located a significant distance from the carbon negative module, energy in the form of transportation is needed to bring the carbon negative renewable resources to the production cite. The sites for the carbon negative module and the production module can be advantageously closely located to one another, or co-located on a single site or even integrated into a single process. It is contemplated that certain output of the carbon negative process can be collected and stored to be used in a production process at a later date. Such storing and subsequent use can be carried out in close proximity to one another, so that significant addition carbon positive activities are not required for its transportation.

In one or more embodiments, the carbon negative module is directly coupled to the production module. By 'directly coupled' it is meant that the two processes are in direct communication with one another, for example, by having piping or tubing that physically connects an output of the carbon negative process with the production module. In other embodiments, the coupling can occur through an intermediary, such electric transmission lines or thermal heat transfer mechanisms, as being within the meaning of 'directly coupled'.

Figure 7:
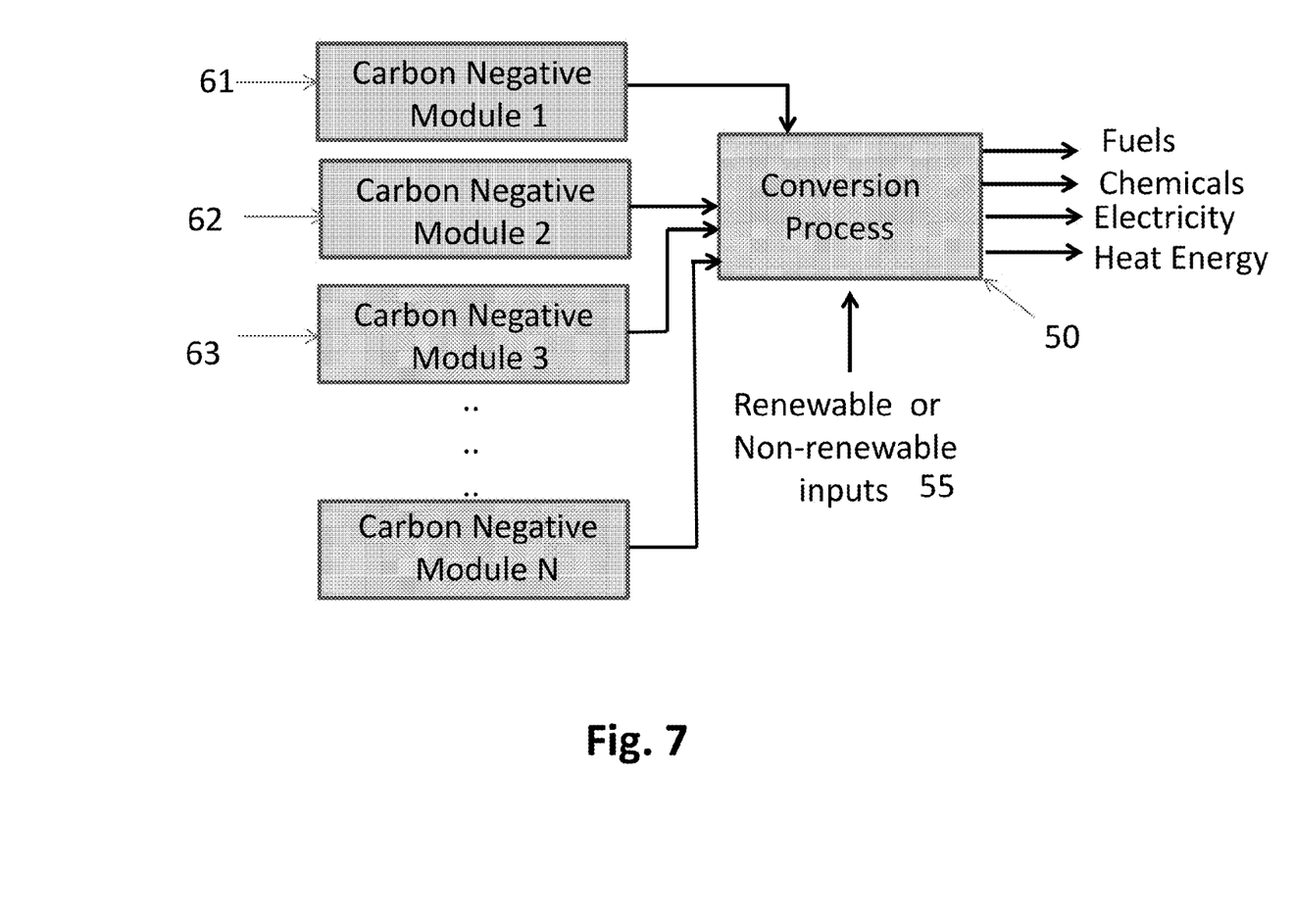
FIG. 7 is a flow diagram illustrating how the output of a plurality of carbon negative process modules can serve as the input to a conversion process.

The relative size carbon negative module 60 to production module 50 determines the degree of carbon negativity and thus carbon remediation applied to the conversion process. If the carbon negative module is relatively small compared to a carbon positive module, then case A as shown in FIG. 2 will be realized. On other hand, if the carbon negative module is sufficiently negative, it can reverse the carbon footprint of a carbon positive production module, as shown in FIG. 3. Instead of one large carbon negative module, an embodiment may have a plurality of carbon negative modules, all feeding into a production module, as shown in FIG. 7. FIG. 7 is an example of a plurality of carbon negative processes producing output in parallel. The input to the production module may be either energy or feedstock as previously discussed. Production module 50 may have additional inputs 55, of renewable or non-renewable form, that allows the conversion process to perform the conversion.

As used herein, the term 'biomass' includes any material derived or readily obtained from plant or animal sources. Such material can include without limitation: (i) plant products such as bark, leaves, tree branches, tree stumps, hardwood chips, softwood chips, grape pumice, sugarcane bagasse, switchgrass; and (ii) pellet material such as grass, wood and hay pellets, crop products such as corn, wheat and kenaf. This term may also include seeds such as vegetable seeds, sunflower seeds, fruit seeds, and legume seeds. The term 'biomass' can also include: (i) waste products including animal manure such as poultry derived waste; (ii) commercial or recycled material including plastic, paper, paper pulp, cardboard, sawdust, timber residue, wood shavings and cloth; (iii) municipal waste including sewage waste; (iv) agricultural waste such as coconut shells, pecan shells, almond shells, coffee grounds; and (v) agricultural feed products such as rice straw, wheat straw, rice hulls, corn stover, corn straw, and corn cobs.

Figure 10:
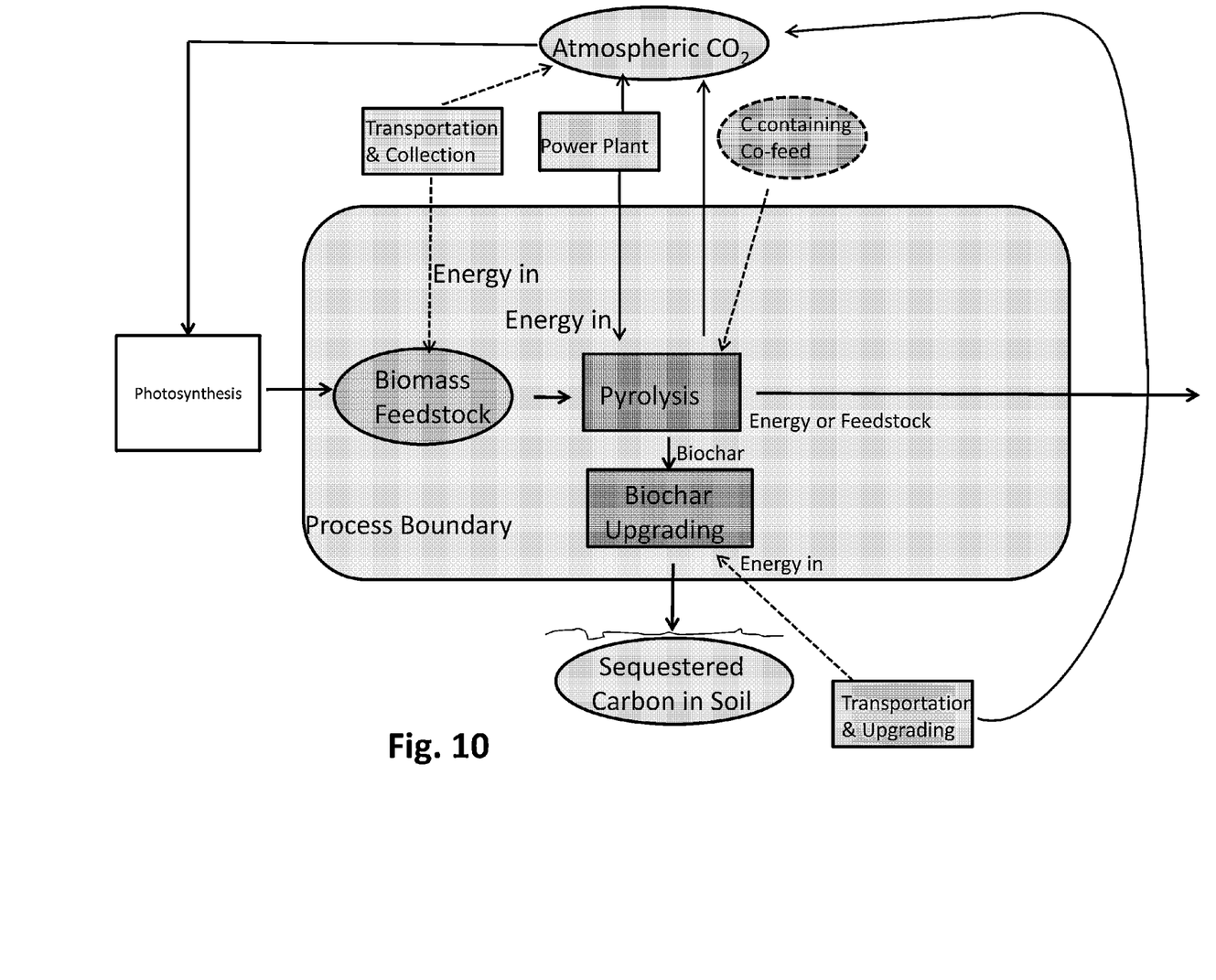
FIG. 10 illustrates carbon balance considerations in determining the carbon negativity aspects of an embodiment carbon negative module.

FIG. 10 is a flow diagram illustrating possible carbon pathways from the point of view of carbon dioxide balance. Atmospheric carbon dioxide is the source of carbon for the photosynthetic process that outputs biomass. Energy is needed to collect and transport biomass, and the production of this energy leaves a carbon footprint. Other carbon footprints are left during the production of energy to effect the conversion of biomass into fuel and sequesterable carbon, energy for the separation and blending processes, and energy for biochar upgrading. The conversion process itself may release carbon dioxide. Sequestered carbon in soil may serve as a small source of carbon dioxide emission, depending on whether the carbon is mixed with compost. In the production of combustible fuel and sequesterable carbon as separate and uncontaminated products, some carbon dioxide is removed from the atmosphere by sequestering carbon in soil. In the case of the present invention, the output path would represent the energy provided to a positive conversion process which could be partly power said conversion process.

Figure 11:
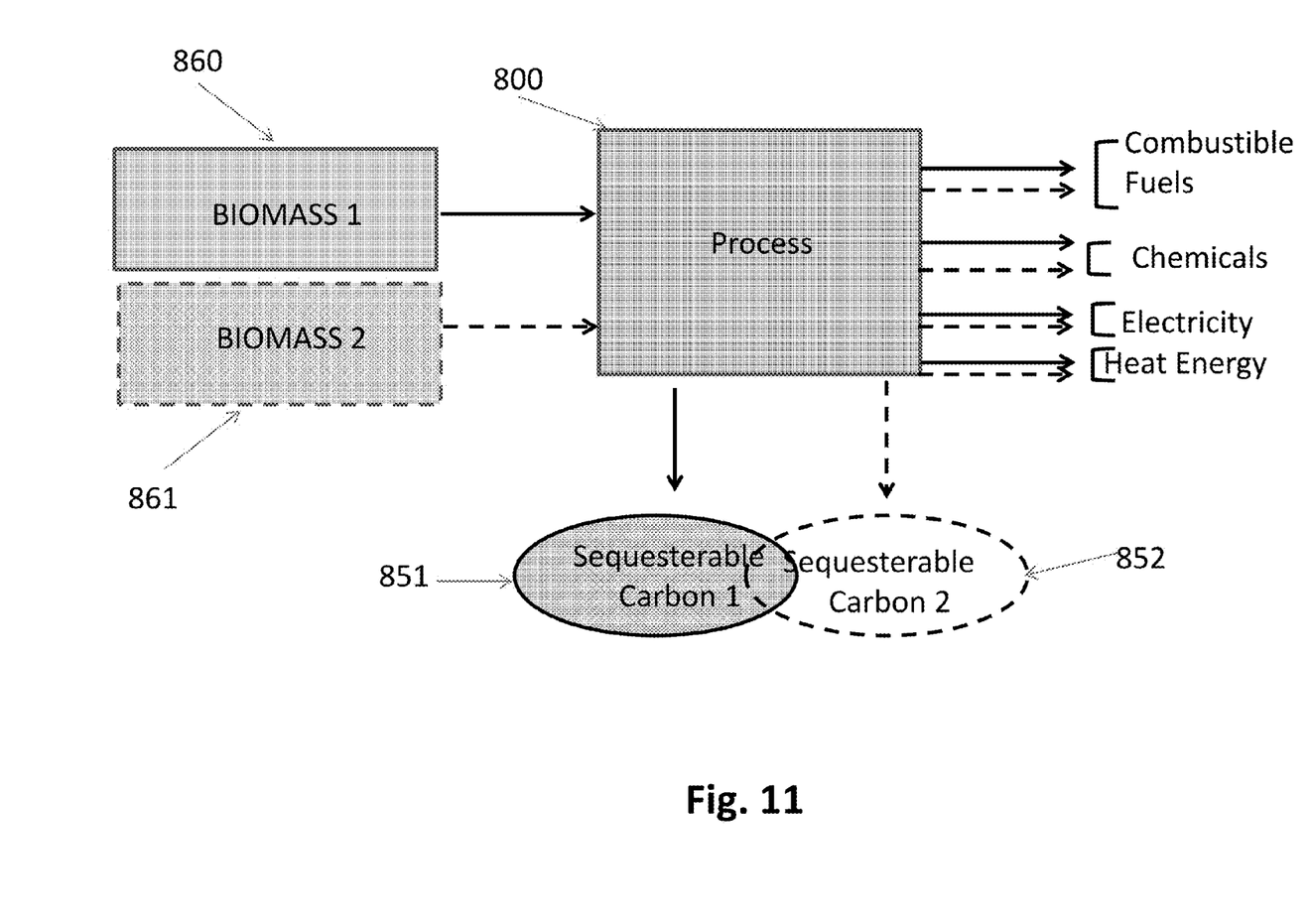
FIG. 11 illustrates an embodiment of the invention in which a negative carbon conversion process is inserted inside a negative carbon conversion process to produce a different type of sequesterable carbon after a different type of biomass is co-fed to the conversion process. Net result is reduction in carbon footprint of the initial carbon negative process.

Carbon remediation may also be effected onto an already existing carbon negative process, as demonstrated by FIG. 6. Conversion process 50 may comprise an already carbon negative process which then takes additional renewable energy from the a distinct carbon negative module. This is illustrated in FIG. 4. In some embodiments, the carbon negative module and the conversion process are the same process, and this demonstrated by FIG. 11. A carbon negative process 800 that takes biomass input 860 to produce sequesterable carbon 851 and outputs chemicals, combustible fuels, electricity and heat energy may be have as additional biomass input 861 (not necessarily the same feedstock as 860) to produce a biochar 852 which produces additional useful outputs. In this manner the carbon footprint of process 800 is further lowered.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. These illustrations and their accompanying description should not be construed as mandating a particular architecture or configuration.

What is claimed is:

1. A method for reducing the carbon footprint of a conversion process, comprising:
    (a) conducting an external carbon negative process having biomass as input and sequesterable carbon and one or both of renewable energy and renewable feedstock as outputs, and
    b) utilizing said renewable energy to at least partly power said conversion process and/or utilizing said renewable feedstock as input to said conversion process.

2. A method according to claim 1 in which the conversion process includes one or more of: electricity production, electrochemical reduction process, smelting, fossil fuel extraction, chemical refining, chemical conversion processes.

3. A method according to claim 1 in which the renewable energy is one or more selected from the group consisting of: heat, combustible biovapors, combustible fuels and electricity.

4. A method according to claim 1 in which electricity is produced by combustion of one or both of combustible biovapors or renewable fuels obtained as output from the carbon negative process.

5. A method according to claim 1 in which the renewable feedstock comprises one or more of light hydrocarbons, C1-C5 light gases, or C6-C20 hydrocarbons.

6. A method according to claim 1 in which the sequesterable carbon is greater than 50% fixed carbon.

7. A method according to claim 1 in which the carbon footprint reduction is greater than 1%.

8. A method according to claim 1 in which the carbon footprint reduction is greater than 10%.

9. The method of claim 1, wherein the sequesterable carbon is sequestered by use as a soil amendment.

10. The method of claim 1, wherein the sequesterable carbon is sequestered by underground storage.

11. The method of claim 1, wherein the sequesterable carbon is sequestered by addition to soil containing compost material.

12. The method of claim 1, wherein the sequesterable carbon is used for carbon offsets.

13. The method of claim 1, wherein the sequesterable carbon is used for carbon credits.

14. A method according to claim 1 in which at least some of the sequesterable carbon is reacted with oxygen, carbon dioxide, methane or steam to generate synthesis gas, which displaces fossil carbon.

15. The method of claim 14, wherein the synthesis gas is converted to combustible fuels, refinery stock or chemicals.

16. The method of claim 15, wherein at least one of the combustible fuels, refinery stock or chemicals is certified as carbon negative.

17. The method of claim 1, wherein the output of a plurality of carbon negative processes serve as input to the conversion process.

18. The method of claim 1 in which the carbon negative process causes the conversion process to qualify for RINs.

19. A system for reducing the carbon footprint of a conversion process, comprising:
    (a) an external carbon negative system having biomass as input and sequesterable carbon and one or both of renewable energy and renewable feedstock as outputs to the conversion process; and
    b) a conversion process directly coupled to the external carbon negative system for receiving one or more of said renewable energy as power in said conversion process and said renewable feedstock as input to said conversion process.

20. A system according to claim 19 in which the size of the carbon negative system is adjustable.

21. A system according to claim 19 in which the carbon negative system produces biochar and biovapors.

22. A system according to claim 19 in which a plurality of external carbon negative system are directly coupled into said conversion process.

23. The system of claim 22, wherein the plurality of external carbon negative systems communicate in parallel with said conversion process.

24. The system of claim 22, wherein the plurality of external carbon negative systems communicate in series with said conversion process.

* * * * *